US010206689B2

(12) United States Patent
Firmbach et al.

(10) Patent No.: US 10,206,689 B2
(45) Date of Patent: Feb. 19, 2019

(54) MEDICAL GUIDING DEVICE

(71) Applicant: Aesculap AG, Tuttlingen (DE)

(72) Inventors: Franz-Peter Firmbach, Emmingen-Liptingen (DE); William Mihalko, Germantown, TN (US); Martin Nonnenmann, Wurmlingen (DE)

(73) Assignee: Aesculap AG, Tuttlingen (DE)

( * ) Notice: Subject to any disclaimer, the term of this patent is extended or adjusted under 35 U.S.C. 154(b) by 386 days.

(21) Appl. No.: 15/086,824

(22) Filed: Mar. 31, 2016

(65) Prior Publication Data

US 2016/0287263 A1 Oct. 6, 2016

Related U.S. Application Data

(60) Provisional application No. 62/142,061, filed on Apr. 2, 2015.

(51) Int. Cl.
*A61B 17/15* (2006.01)
*A61B 90/00* (2016.01)

(52) U.S. Cl.
CPC ............ *A61B 17/157* (2013.01); *A61B 17/15* (2013.01); *A61B 2090/376* (2016.02); *A61B 2090/3966* (2016.02)

(58) Field of Classification Search
CPC .................................................... A61B 17/157
See application file for complete search history.

(56) References Cited

U.S. PATENT DOCUMENTS

| 4,938,762 | A  | * | 7/1990 | Wehrli | A61B 17/154 |
| | | | | | 606/88 |
| 6,712,824 | B2 | * | 3/2004 | Millard | A61B 17/154 |
| | | | | | 606/87 |
| 7,241,298 | B2 | * | 7/2007 | Nemec | A61B 17/15 |
| | | | | | 606/86 R |
| 7,520,880 | B2 | * | 4/2009 | Claypool | A61B 17/155 |
| | | | | | 606/246 |
| 7,794,467 | B2 | | 9/2010 | McGinley et al. | |

(Continued)

FOREIGN PATENT DOCUMENTS

DE 19516294 11/1996
EP 1442712 8/2004

(Continued)

*Primary Examiner* — Zade Coley
(74) *Attorney, Agent, or Firm* — Lipsitz & McAllister, LLC

(57) ABSTRACT

In a first aspect of the invention relates to a medical guide device for working on a bone. This guide device includes a holding arrangement, which is holdable firmly against a bone, for holding the guide device firmly against the bone and a saw template with a guide slot for a saw blade. In an adjustment position, the holding arrangement and the saw template engage with one another and are arranged to be movable in relation to one another. The holding arrangement and the saw template are movable from the adjustment position into a sawing position in which they are held firmly and immovably in relation to one another. Said guide device includes a coupling arrangement for coupling the holding arrangement and the saw template in the adjustment position and in the sawing position.

22 Claims, 13 Drawing Sheets

(56) References Cited

U.S. PATENT DOCUMENTS

| | | | |
|---|---|---|---|
| 8,118,811 B2* | 2/2012 | Coon | A61B 17/155 606/86 R |
| 2002/0133163 A1* | 9/2002 | Axelson, Jr. | A61B 17/154 606/88 |
| 2004/0122436 A1* | 6/2004 | Grimm | A61B 17/157 606/87 |
| 2006/0235290 A1* | 10/2006 | Gabriel | A61B 17/157 600/407 |
| 2007/0100346 A1 | 5/2007 | Wyss et al. | |
| 2007/0173849 A1* | 7/2007 | Claypool | A61B 17/155 606/87 |
| 2010/0064216 A1* | 3/2010 | Borja | A61B 17/157 715/705 |
| 2010/0121334 A1 | 5/2010 | Couture et al. | |
| 2012/0109228 A1 | 5/2012 | Boyer et al. | |

FOREIGN PATENT DOCUMENTS

| | | |
|---|---|---|
| EP | 1779790 | 5/2007 |
| WO | 2005/048851 | 6/2005 |
| WO | 2010/128409 | 11/2010 |

* cited by examiner

MEDICAL GUIDING DEVICE

CROSS-REFERENCE TO RELATED APPLICATIONS

This application claims the benefit of U.S. provisional patent application No. 62/142,061 filed on Apr. 2, 2015, which is incorporated herein by reference in its entirety and for all purposes.

FIELD OF THE INVENTION

The present invention relates to medical guide devices for working on a bone generally, and more specifically to a medical guide device for working on a bone, this guide device including a holding arrangement for holding the guide device firmly against the bone and a saw template with a guide slot for a saw blade, wherein, in an adjustment position, the holding arrangement and the saw template engage with one another and are arranged to be movable in relation to one another, wherein the holding arrangement and the saw template are movable from the adjustment position into a sawing position in which they are held firmly and immovably in relation to one another, this guide device including a coupling arrangement for coupling the holding arrangement and the saw template in the adjustment position and in the sawing position.

BACKGROUND OF THE INVENTION

Medical guide devices of the type mentioned in the introduction are used in particular in surgery to prepare bone surfaces against which abutment surfaces of an endoprosthesis are brought into abutment. In this context, the holding arrangement is conventionally first held firmly against the bone that is to be prepared. For example, for preparing an implant of a knee joint endoprosthesis the holding device is held firmly against a tibia or femur. In a next step, a saw template that is for example coupled to the holding arrangement can be oriented in relation thereto. Thereafter, with the aid of the saw template, one or more cuts may be made to the bone, for example using an oscillating saw whereof the saw blade is guided through the saw template.

It is a particular problem, in medical guide devices of the type mentioned in the introduction, to secure them to the bone quickly and simply and to orient the saw template in the desired manner.

SUMMARY OF THE INVENTION

In a first aspect of the invention a medical guide device for working on a bone is provided. This guide device includes a holding arrangement, which is holdable firmly against a bone, for holding the guide device firmly against the bone and a saw template with a guide slot for a saw blade. In an adjustment position, the holding arrangement and the saw template engage with one another and are arranged to be movable in relation to one another. The holding arrangement and the saw template are movable from the adjustment position into a sawing position in which they are held firmly and immovably in relation to one another. Said guide device includes a coupling arrangement for coupling the holding arrangement and the saw template in the adjustment position and in the sawing position. The coupling arrangement includes first and second coupling elements which are arranged or constructed on the one hand on the holding arrangement and on the other on the saw template, are in engagement with one another in the adjustment position, and are held against one another with at least one of force locking and positive locking in the sawing position.

BRIEF DESCRIPTION OF THE DRAWINGS

The foregoing summary and the following description may be better understood in conjunction with the drawing figures, of which.

DETAILED DESCRIPTION

Figure 1:
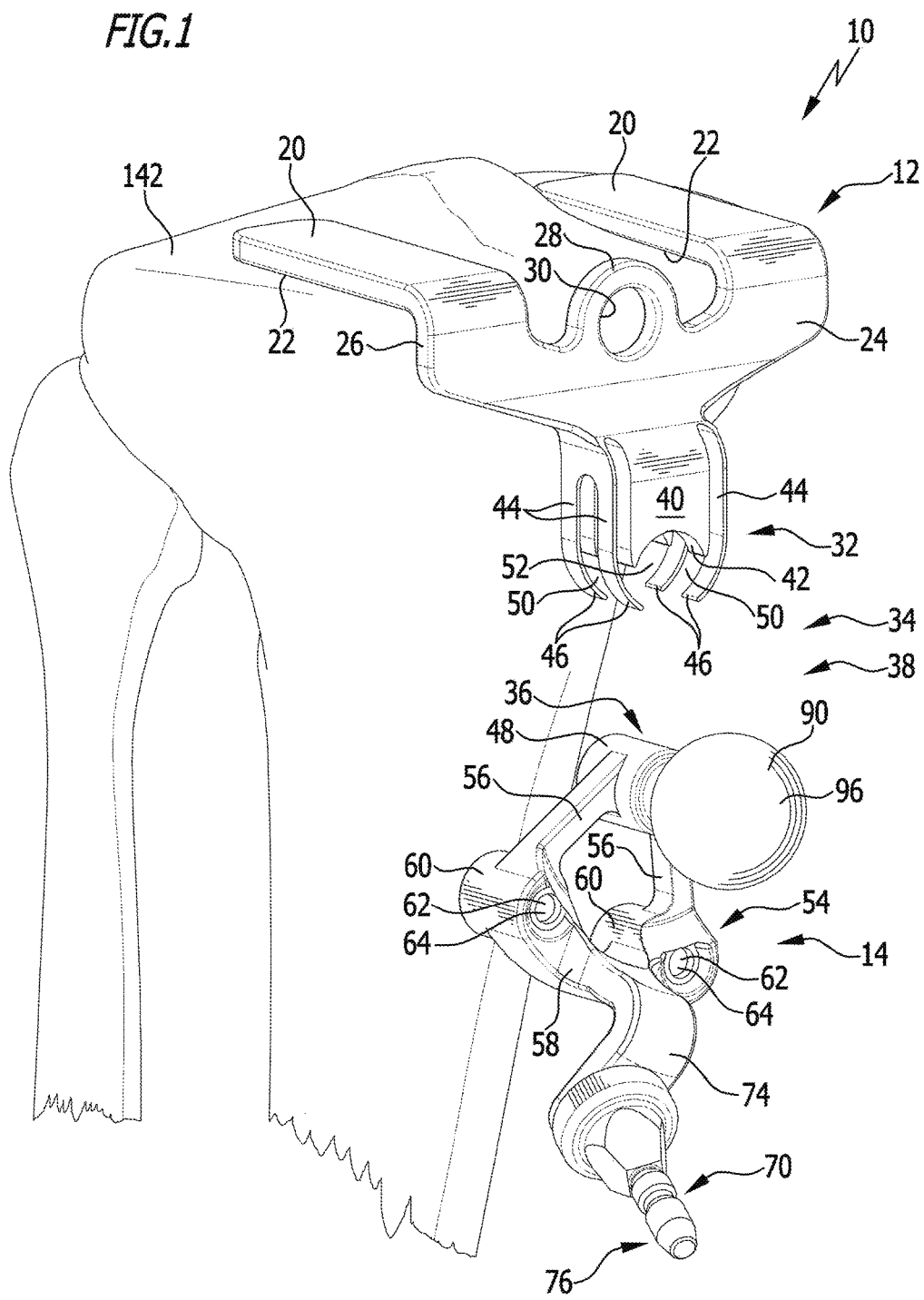
FIG. 1 shows a perspective illustration of a positioning arrangement, in abutment against a bone, of a medical guide device before it is brought into engagement with a holding arrangement.
Figure 2:
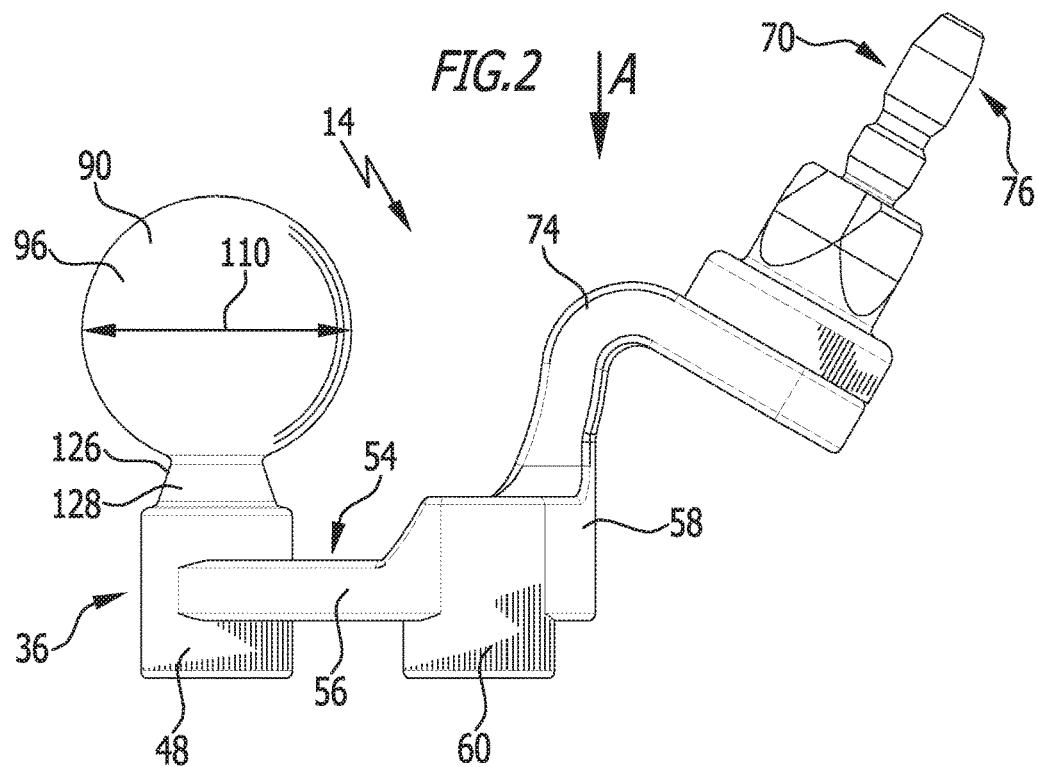
FIG. 2 shows a side view of the holding arrangement from FIG. 1.
Figure 3:
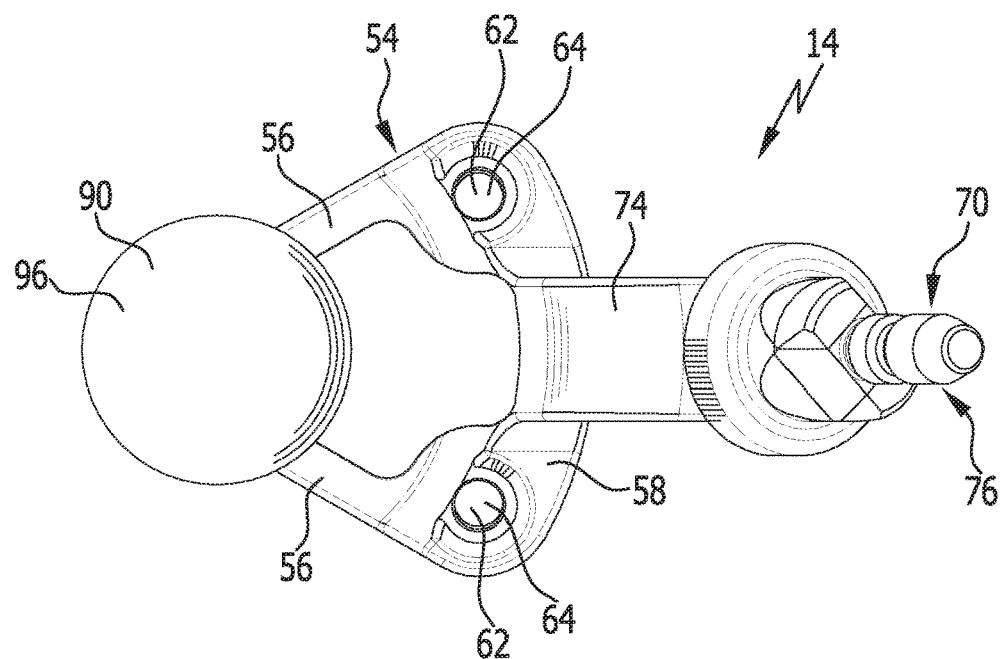
FIG. 3 shows a view of the holding arrangement from FIG. 2, in the direction of the arrow A.

Although the invention is illustrated and described herein with reference to specific embodiments, the invention is not intended to be limited to the details shown. Rather, various modifications may be made in the details within the scope and range of equivalents of the claims and without departing from the invention.

The present invention relates to a medical guide device for working on a bone, this guide device including a holding arrangement, which is holdable firmly against a bone, for holding the guide device firmly against the bone and a saw template with a guide slot for a saw blade, wherein, in an adjustment position, the holding arrangement and the saw template engage with one another and are arranged to be movable in relation to one another, wherein the holding arrangement and the saw template are movable from the adjustment position into a sawing position in which they are held firmly and immovably in relation to one another, this guide device including a coupling arrangement for coupling the holding arrangement and the saw template in the adjustment position and in the sawing position, wherein the coupling arrangement includes first and second coupling elements which are arranged or constructed on the one hand on the holding arrangement and on the other on the saw template, are in engagement with one another in the adjustment position, and are held against one another with at least one of force locking and positive locking in the sawing position.

A medical guide device having a coupling arrangement of this kind makes it possible, in the adjustment position, to orient the saw template in relation to the holding arrangement and, once the holding arrangement is held firmly against the bone, to orient the saw template in relation to the bone in a defined manner. Once the saw template is oriented as desired, the coupling arrangement makes it possible to transfer the first and second coupling elements from the adjustment position to the sawing position in order to hold the saw template in the latter in the defined orientation, such that a saw cut for working on the bone may be performed with a high degree of precision. The proposed guide device thus in particular makes it possible first to position the holding arrangement on the bone approximately, optionally also with the saw template held movably on the holding arrangement, and only then to carry out a fine orientation of the saw template.

In order to enable positioning and/or orientation of the saw template to be carried out with a high degree of precision, it is favourable if there is arranged or constructed on the holding arrangement and/or on the saw template an interface for a medical referencing arrangement whereof the position and/or orientation in space is detectable by a medical navigation system, and/or in that a medical referencing arrangement whereof the position and/or orientation in space is detectable by a medical navigation system is arranged or constructed on the holding arrangement and/or the saw template. The proposed further development in particular enables a position and/or orientation of the holding arrangement and/or the saw template to be determined with a high degree of precision by means of a navigation system. Once, in particular, a positioning and/or orientation of the holding arrangement on the bone that is to be worked on is known, the saw template can accordingly be oriented in relation to the holding arrangement as desired, such that the bone surfaces can be prepared exactly in order to firmly hold against them, temporarily or permanently, implant parts of a prosthesis to be implanted.

It is advantageous if the interface is constructed in the form of a first connecting element which is constructed to correspond to a second connecting element of the medical referencing arrangement, and if the first and the second connecting element are in engagement in a connected position and are disengaged in a cleaning position. An interface of this kind makes it possible in particular to completely separate the referencing arrangement from the holding arrangement and/or the saw template. This has advantages when cleaning all the components after a surgical procedure. Further, it also offers the possibility of removing the referencing arrangement from the holding arrangement and/or from the saw template before a saw cut is performed. After removal, in particular in the case of restricted spatial conditions in the region of the operation site, the referencing arrangement is no longer in the way of the person performing the operation.

A referencing arrangement may be connected to the holding arrangement and/or the saw template in a simple manner if the first connecting element is constructed in the form of a connecting projection or a connection receptacle. In that case a corresponding connecting element may in particular be constructed on the referencing arrangement in order to connect, preferably in a unique orientation relative to one another, the referencing arrangement to the holding arrangement and/or the saw template.

Favourably, the medical referencing arrangement bears at least one marker element whereof the position in space is detectable by a medical navigation system. Preferably, the medical referencing arrangement includes two, three, four or indeed more marker elements. The greater the number thereof, the more precisely a position and/or an orientation of the referencing arrangement in space may be detected by the navigation system.

According to a further preferred embodiment of the invention, it may be provided for the coupling arrangement to be constructed such that, in the adjustment position, the saw template and the holding arrangement are mounted on one another such that they are displaceable in relation to one another. This embodiment thus defines at least one degree of translational freedom in order to move the saw template in at least one direction relative to the holding arrangement.

It is further advantageous if the second coupling element defines a coupling element longitudinal axis, and if, in the adjustment position, the saw template and the holding arrangement are mounted on one another such that they are displaceable in relation to one another parallel to the coupling element longitudinal axis. In this way, by means of a corresponding embodiment, a defined guidance may be predetermined for a displacement movement, in particular parallel to the coupling element longitudinal axis.

It is favourable if the coupling arrangement is constructed such that, in the adjustment position, the saw template and the holding arrangement are mounted on one another such that they are pivotal in relation to one another about a pivot axis. This embodiment makes it possible in particular to predetermine an inclination of the guide slot in a desired manner, for example in relation to the bone against which the guide device is firmly held, or in relation to the holding arrangement. It goes without saying that the coupling arrangement may also define two or three or more pivot axes that do not run parallel to one another. This makes it possible in particular to orient the saw template in relation to the holding arrangement about a plurality of degrees of freedom in relation to one another in a desired manner.

It is particularly advantageous if the coupling arrangement is constructed such that, in the adjustment position, the saw template and the holding arrangement are mounted on one another such that they are rotatable in relation to one another about an axis of rotation. This embodiment may also be provided in particular in combination with mounting the first and second coupling elements such that they are displaceable in relation to one another. A rotatable mounting about an axis of rotation makes it possible in particular to orient the saw template relative to the holding arrangement simply and precisely.

The coupling arrangement may be constructed in a particularly simple manner if it includes a ball joint.

It is favourable if the first coupling element is constructed in the form of a joint ball and the second coupling element is constructed in the form of a joint ball receptacle. The joint ball and the joint ball receptacle are preferably dimensioned such that rotation, at least in the adjustment position, relative to one another is possible about a common axis of rotation.

Advantageously, the joint ball receptacle defines a hollow cylindrical or substantially hollow cylindrical internal contour. A joint ball receptacle of this kind makes it possible in particular not only to rotate a joint ball held therein about a centre point defined by the joint ball but also to displace the joint ball relative to the joint ball receptacle parallel to a longitudinal axis defined by the joint ball receptacle. Thus, a plurality of degrees of freedom, which make it possible to orient the saw template relative to the holding arrangement simply and in a defined manner, may be predetermined in a simple manner.

In order to make the structure of the guide arrangement as simple as possible, it is favourable if the joint ball receptacle includes at least two hollow cylindrical wall portions that define an internal diameter that corresponds or substantially corresponds to an external diameter of the joint ball. The dimensions are preferably selected such that, in the adjustment position, movement of the joint ball and the joint ball receptacle is possible relative to one another.

A particularly compact structure of the holding arrangement can in particular be achieved in that it has a holding arrangement base body, and in that the first coupling element is held on the holding arrangement base body. This makes it possible, for example, to hold the holding arrangement base body firmly against a bone and to bring the second coupling element of the saw template into engagement with the first coupling element.

According to a further preferred embodiment of the invention, it may be provided for a narrowed portion or a connecting web to be constructed between the first coupling element and the holding arrangement base body, and, in the adjustment position and the coupling position, for the narrowed portion or connecting web to pass through a coupling gap in the joint ball receptacle. As a result of this particular embodiment, in particular a joint ball may be brought into engagement in a defined manner with one of the above-described advantageous joint ball receptacles. Further, an approximate guidance may moreover be created between the two coupling elements if the coupling gap corresponds substantially to the external dimensions of the narrowed portion, such that the narrowed portion is only movable in relation to the second coupling element parallel to a longitudinal axis thereof.

Further, it may be advantageous if the guide arrangement includes a fixing arrangement for holding the holding arrangement and the saw template in the sawing position with force locking and/or positive locking. In particular, the fixing arrangement makes it possible in a simple way to transfer the guide device from the adjustment position to the sawing position and/or vice versa.

The saw template and the holding arrangement may be held firmly against one another in the sawing position in a particularly simple way if the fixing arrangement is constructed in the form of a latching, snap-fitting and/or clamping arrangement.

The fixing arrangement can be constructed to be particularly simple and compact if it includes at least one first fixing element which, in the sawing position, presses the first coupling element directly or indirectly against the second coupling element. In particular, in this way clamping of the coupling elements against one another may be achieved simply and reliably.

It is advantageous if the fixing arrangement includes at least one second fixing element, and if, in the sawing position, the at least one first fixing element presses the at least one second fixing element against the first coupling element and presses the latter against the second coupling element. In this way, a contact pressure force may be transmitted indirectly from the first fixing element by way of the second fixing element to the first and/or second coupling element.

In order to enable a holding force for holding the holding arrangement and the saw template against one another already in the adjustment position, it is favourable if the at least one second fixing element includes a leaf spring element that is arranged or constructed on the saw template. The leaf spring element—other types of spring element also being conceivable—in particular makes it possible to exert a defined contact pressure or clamping force already in the adjustment position in order to hold the holding arrangement and the saw template against one another in a defined manner.

Preferably, the at least one second fixing element includes a contact pressure body. The latter may in particular be formed from a correspondingly suitable material or be constructed to be sufficiently non-deformable for it to be possible to exert a defined clamping force by means of the fixing arrangement in order to hold the holding arrangement and the saw template against one another in the adjustment position and/or the sawing position.

It is advantageous if the leaf spring element bears, at a free end or in the region of a free end, the contact pressure body. This construction in particular makes it possible to press the contact pressure body, by means of the leaf spring element, directly or indirectly against the first and/or second coupling element in a defined manner.

In order to enable a particularly compact structure of the fixing arrangement, it is favourable if the contact pressure body defines a contact pressure body longitudinal axis that runs parallel or substantially parallel to the coupling element longitudinal axis. For example, the contact pressure body may be arranged with its contact pressure body longitudinal axis in the coupling gap and oriented parallel thereto.

For particularly simple and intuitive handling of the guide arrangement, it is advantageous if the at least one second fixing element is arranged or constructed to be movable on the saw template. If for example the holding arrangement is already held firmly against the bone, a person performing the operation need merely hold the saw template and, by moving the at least one second fixing element, can transfer the saw template and the holding arrangement from the adjustment position to the sawing position.

A particularly compact structure of the guide device can in particular be achieved in that the at least one second fixing element is held in a gap or a recess between the at least two hollow cylindrical wall portions. In particular, the gap may be a or the above-described coupling gap. For example, one, two or more contact pressure bodies may be arranged between the two hollow cylindrical wall portions.

For simple and intuitive actuation of the guide device, it is favourable if the at least one first fixing element includes an eccentric body that is pivotal about an eccentric pivot axis. By simply pivoting the eccentric body about the eccentric pivot axis, it is thus possible to transfer the guide device from the adjustment position to the sawing position and/or vice versa. Providing an eccentric body in the manner described makes it possible in particular to vary continuously a clamping force between the cooperating coupling elements of the coupling arrangement. Moreover, using a coupling arrangement of this kind, all the degrees of freedom of the coupling arrangement may be blocked, in particular by a simple pivotal movement of the eccentric body. Thus, different adjustment screws or similar are not required to orient the saw template and the holding arrangement relative to one another in a desired manner, but rather merely a simple pivoting of the eccentric body about the eccentric pivot axis.

In order to achieve optimum clamping of the coupling elements of the coupling arrangement against one another, it is advantageous if the eccentric axis runs transversely, in particular perpendicular, to the coupling element longitudinal axis. In particular, the eccentric axis may run perpendicular to the coupling element longitudinal axis.

Further, it may be favourable if the eccentric axis runs parallel or substantially parallel to the guide slot. In particular, the at least one first fixing element may be arranged or constructed such that in the adjustment position the guide slot is covered by the at least one first fixing element, and in the sawing position the at least one first fixing element uncovers the guide slot of the saw template. In this way, it may be ensured in particular that a saw cut is only carried out if the saw template is held reliably against the holding arrangement in the sawing position.

In order to enable simple handling of the fixing arrangement, it is favourable if the at least one first fixing element includes an actuating member. Preferably, the actuating member is arranged or constructed in particular to project away from the eccentric body. For example, it may be constructed to be tab-shaped or lug-shaped, such that a person performing the operation can pivot the eccentric body in a simple manner in order to transfer the guide device from the adjustment position to the sawing position and/or vice versa.

So that the guide device can be held firmly against a bone in a defined manner, it is advantageous if at least one securing element receptacle for a bone securing arrangement is arranged or constructed on the holding arrangement and/or the saw template. For example, the at least one securing element receptacle may be constructed for receiving one or more securing elements, for example in the form of bone screws or bone nails or similar.

The at least one securing element receptacle can be constructed in a particularly simple manner if it is constructed in the form of an aperture. For example, the aperture may be constructed in the form of a bore. A receptacle of this kind may be constructed both on the holding arrangement and on the saw template in a simple manner and with the desired precision.

Advantageously, the holding arrangement has at least two securing element receptacles. Preferably, the longitudinal axes of the at least two securing element receptacles run parallel or substantially parallel to one another. As an alternative, the longitudinal axes may also run in a manner inclined with respect to one another. At least one securing element may be guided through each of the at least two securing element receptacles in order to hold the holding arrangement firmly against a bone, at least temporarily, in a defined and stable manner.

Further, it may be advantageous if the saw template has at least two securing element receptacles whereof the longitudinal axes run in a manner inclined with respect to one another. The longitudinal axes may also selectively run parallel to one another. In each case, the at least two securing element receptacles of the saw template make it possible likewise to hold the latter firmly against a bone, at least temporarily, for example using securing elements suitable therefor.

For a particularly stable embodiment of the guide device, it is favourable if the saw template includes a saw template base body on which the guide slot is arranged or constructed.

According to a further preferred embodiment of the invention, it may be provided for the guide arrangement to include a positioning arrangement which is coupled to the holding arrangement in a positioning disposition. By means of the positioning arrangement that is coupled to the holding arrangement in the positioning disposition, the holding arrangement may be positioned on the bone in a simple and defined manner. The positioning arrangement may selectively be completely separable from the holding arrangement, such that it is only used for positioning the holding arrangement on the bone but can be completely removed while at least one saw cut is being carried out.

It is advantageous if the positioning arrangement includes at least one bone abutment element having a bone abutment surface and at least one first coupling element of a coupling arrangement, wherein, in the positioning disposition, the at least one first coupling element is in engagement with force and/or positive locking with at least one second coupling element of the coupling arrangement that is arranged or constructed on the holding arrangement. A coupling arrangement of this kind makes it possible in particular to connect the positioning arrangement and the holding arrangement to one another and where appropriate also to release them from one another again.

The positioning arrangement and the holding arrangement may be coupled to one another, at least temporarily, particularly quickly and simply if the coupling arrangement is constructed in the form of a latching and/or snap-fitting connecting arrangement. For example, in this way the positioning arrangement may be grasped and coupled to the holding arrangement. In particular, the positioning arrangement may be clipped onto the holding arrangement.

The coupling arrangement may be constructed to be particularly simple and compact if the at least one second coupling element is constructed in the form of a cylindrical coupling body, and if the at least one first coupling element is constructed in the form of a coupling receptacle corresponding to the coupling body. In particular, the cylindrical coupling body may bear or include the first coupling element. Thus, it is in particular possible to couple the holding arrangement and the positioning arrangement to one another such that the first coupling element is at least temporarily associated with both arrangements.

FIG. 1 illustrates schematically part of a medical guide device, which as a whole is designated by the reference numeral 10, namely a positioning arrangement 12 and a holding arrangement 14. Further, the medical guide device includes a saw template 16 having a guide slot for a saw blade, for example an oscillating saw.

The positioning arrangement 12 includes two plate-shaped bone abutment elements 20 which each define a bone abutment surface 22. The two bone abutment surfaces 22 define a common abutment plane.

The bone abutment elements 20 form, with a cross piece 24, a substantially U-shaped abutment body 26. The cross piece 24 is formed from a flat material. The two bone abutment elements 20 are constructed in one piece with the cross piece 24 and are formed by being bent through 90°.

The cross piece 24 further has a holding tab 28 which is in the shape of a substantially semi-circular disc and is provided with a circular aperture 30, and which projects in the direction of the plane defined by the bone abutment surfaces 22.

Figure 4:
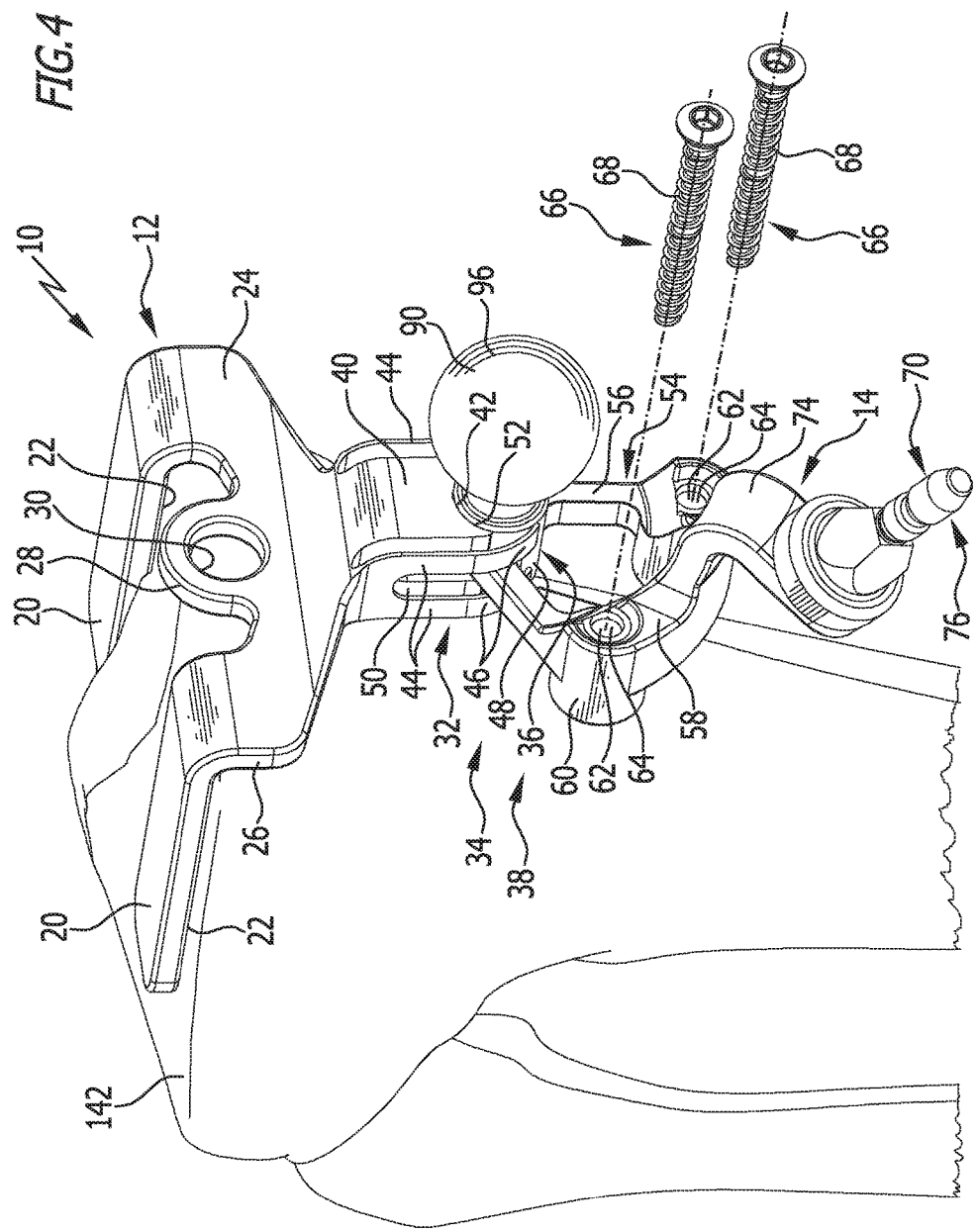
FIG. 4 shows a schematic perspective view of the coupled-together positioning arrangement and holding arrangement before the holding arrangement is held firmly against the bone by means of two bone screws.
Figure 5:
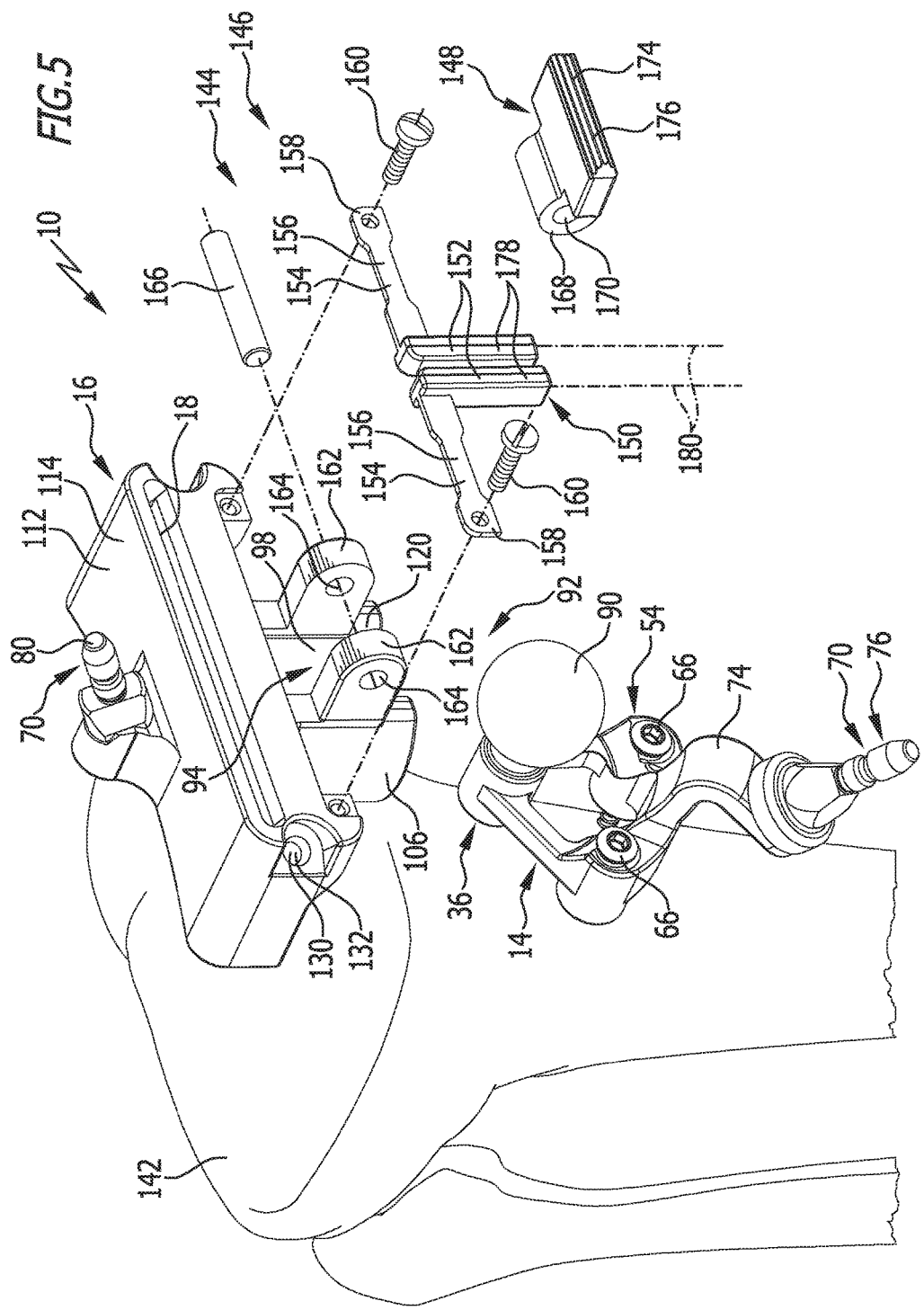
FIG. 5 shows a schematic perspective view of the holding arrangement held firmly against the bone, with an exploded illustration of a saw template.
Figure 6:
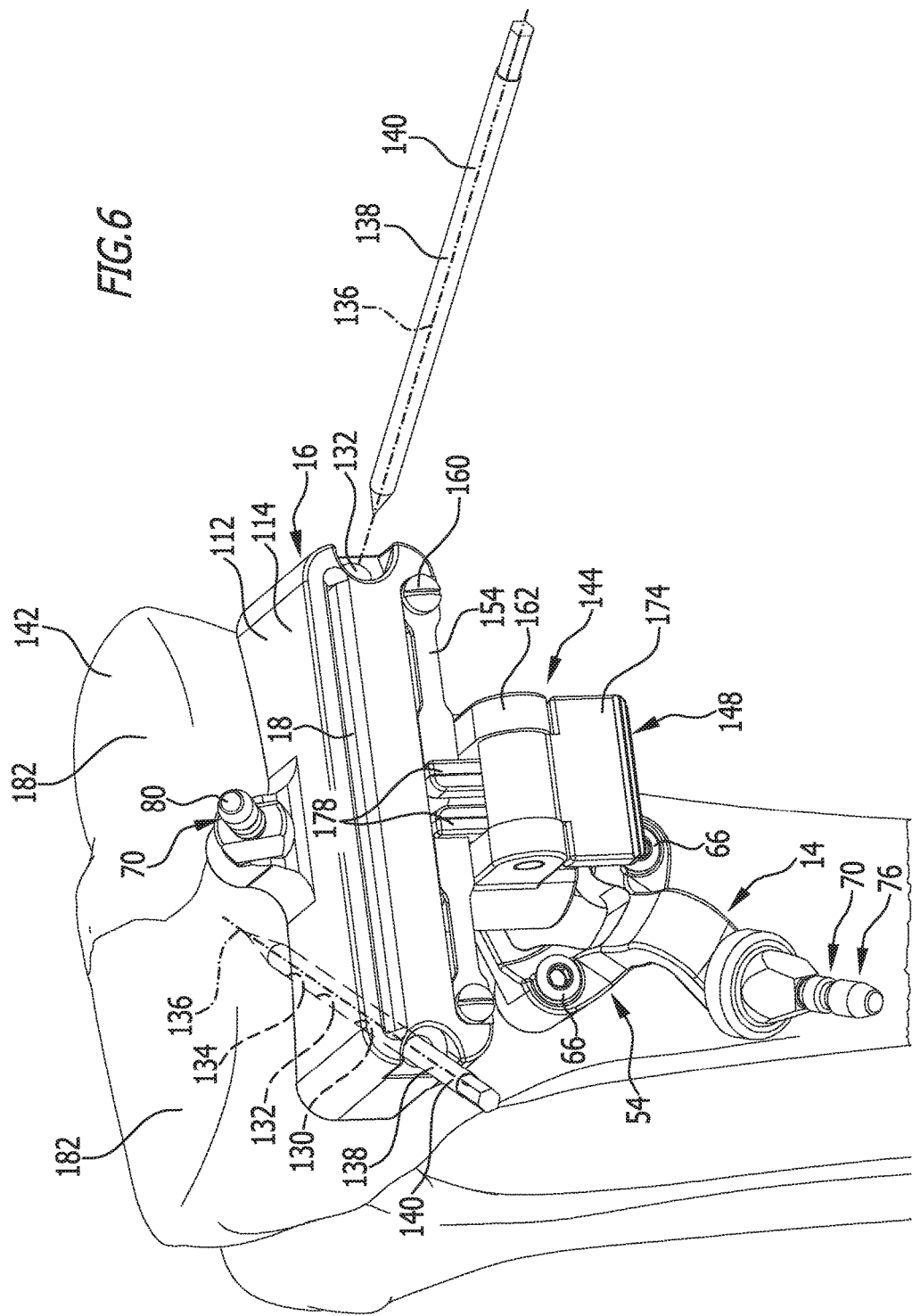
FIG. 6 shows a schematic perspective illustration of a holding arrangement, held firmly against the bone and with a saw template coupled thereto, in the sawing position, with the saw template held firmly against the bone by means of two bone pins.

Further projecting from the cross piece 24, in a direction pointing away from the holding tab 28, is a first coupling element 32 of a coupling arrangement which as a whole is designated by the reference numeral 34, this first coupling element 32 engaging, in a positioning disposition, as illustrated by way of example in FIG. 4, with force locking and/or positive locking with a second coupling element 36 that is arranged or constructed on the holding arrangement 14.

The coupling arrangement 34 is constructed in the form of a latching and/or snap-fitting connecting arrangement 38. The first coupling element 32 includes two flat holding bodies 40 that project parallel to the cross piece 24 and each have, directed away from the respective holding body 40, a concavely curved abutment surface 42 which defines a cutout in a hollow cylindrical surface.

Transversely in relation to the holding bodies 40 and laterally surrounding the latter, two leaf spring elements 44 are integrally formed on the cross piece 24 with in each case two curved ends 46 directed towards one another.

The abutment surfaces 42 and the ends 46 substantially define a hollow cylindrical contour for receiving the second coupling element 36, which is constructed in the form of a right circular cylinder 48. The leaf spring elements 44 each define a gap 50 between the ends 46.

Thus, the second coupling element 36 is constructed in the form of a cylindrical coupling body, and the first coupling element 32 is constructed in the form of a coupling receptacle 52 corresponding to the circular cylinder 48.

The holding arrangement 14 includes a holding arrangement base body 54 which includes the circular cylinder 48. Two limbs 56 extend from there, perpendicular to a longitudinal axis of the circular cylinder 48 and angled with respect to one another about an internal angle of approximately 60°, to a slightly convexly curved cross piece 58 that is directed away from the circular cylinder 48.

The limbs 56 and the cross piece 58 are connected to one another in each case via a cylindrical body 60 which is provided, parallel to a longitudinal axis thereof, with a bore 62. Each bore defines a securing element receptacle 64, through each of which a securing element 66 is passable, at least in part. FIG. 4 illustrates, by way of example, two bone screws 68 as the securing elements 66, whereof shafts provided with an external thread have an external diameter that is adapted to an internal diameter of the securing element receptacles 64.

Figure 7:
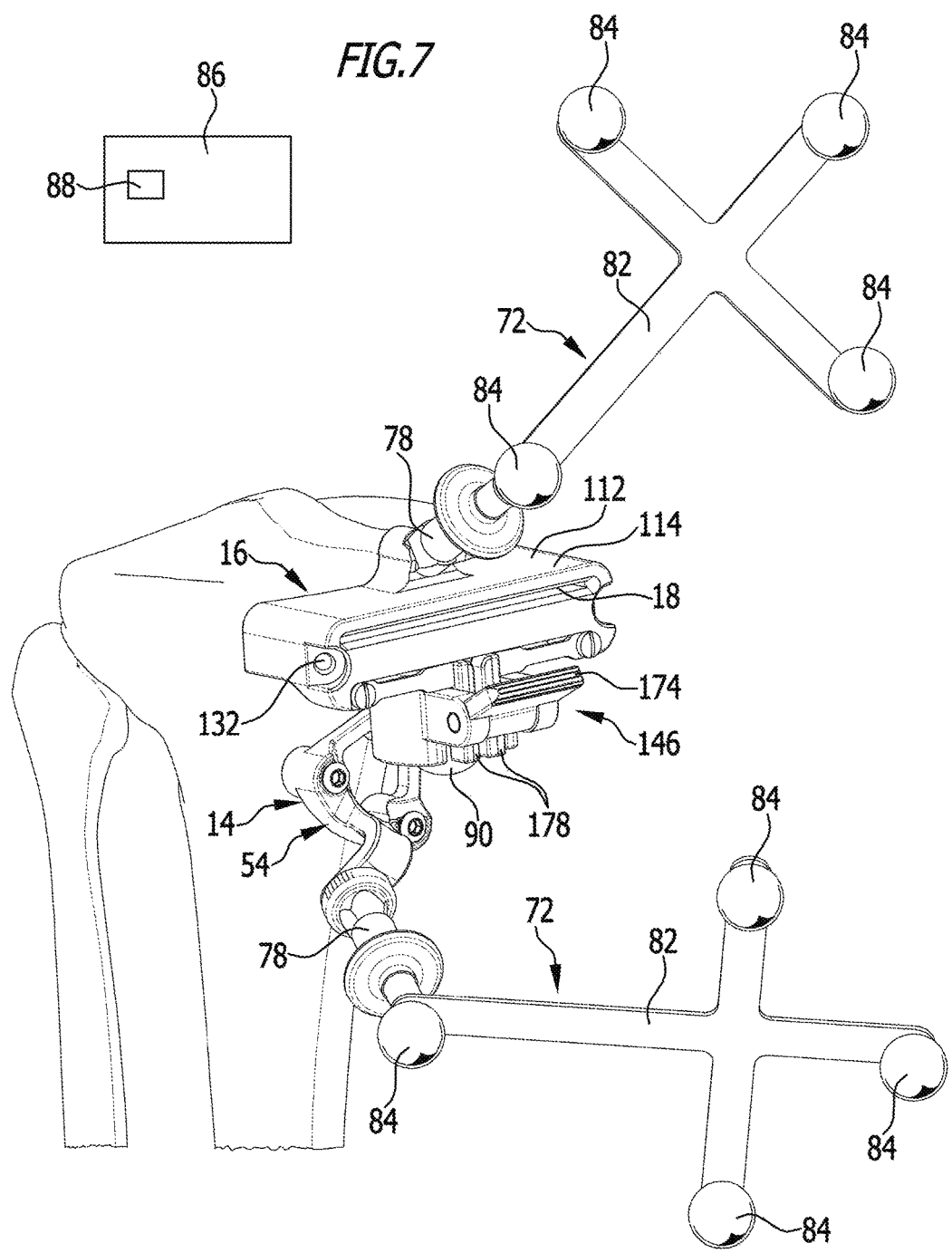
FIG. 7 shows a schematic perspective view of the holding arrangement, held firmly against the bone and with a saw template coupled thereto, in the adjustment position, wherein both the saw template and the holding arrangement are each connected to a referencing arrangement.
Figure 8:
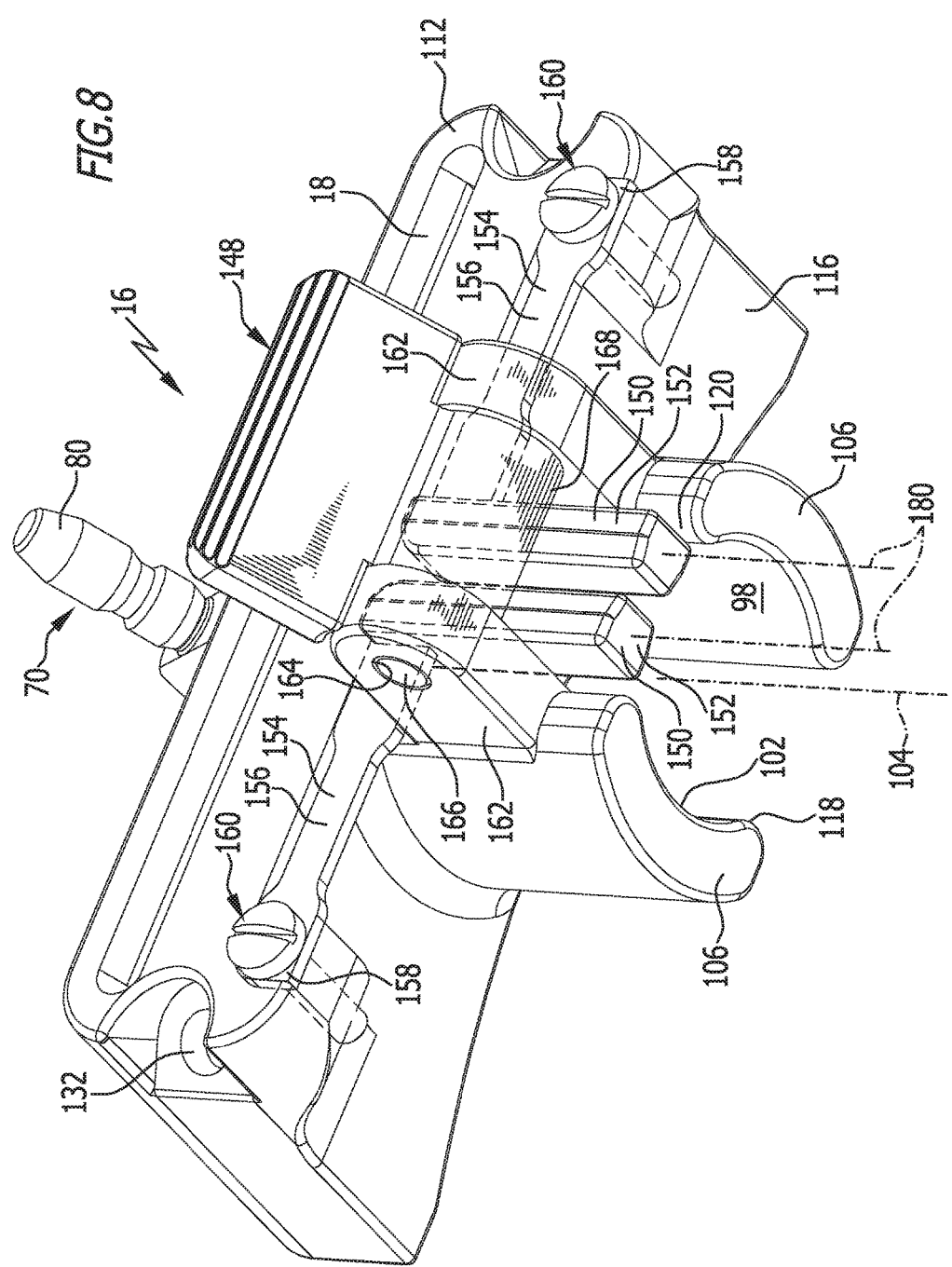
FIG. 8 shows a perspective and partly transparent view of the saw template in the adjustment position.
Figure 9:
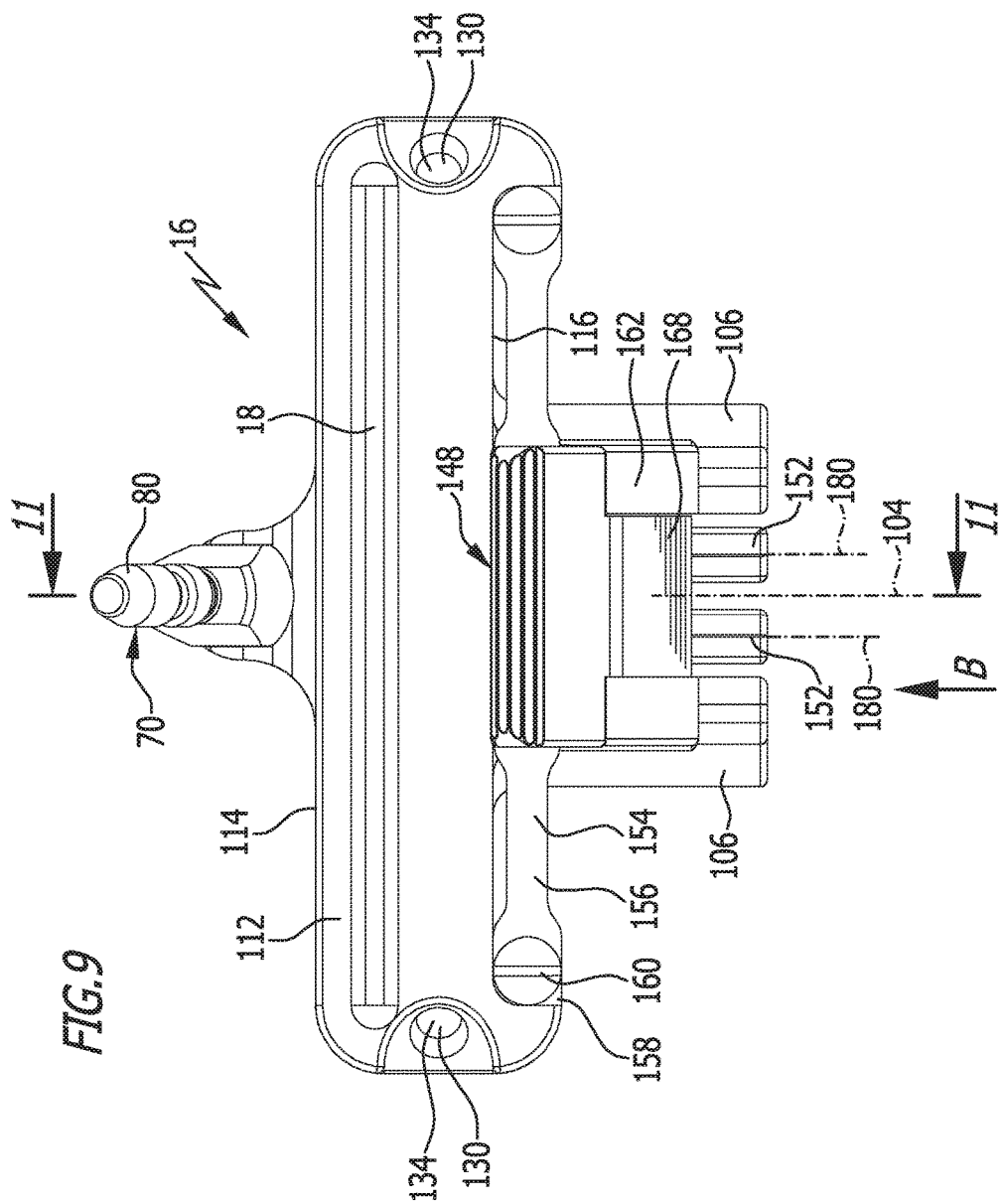
FIG. 9 shows a plan view of the saw template from FIG. 8.
Figure 10:
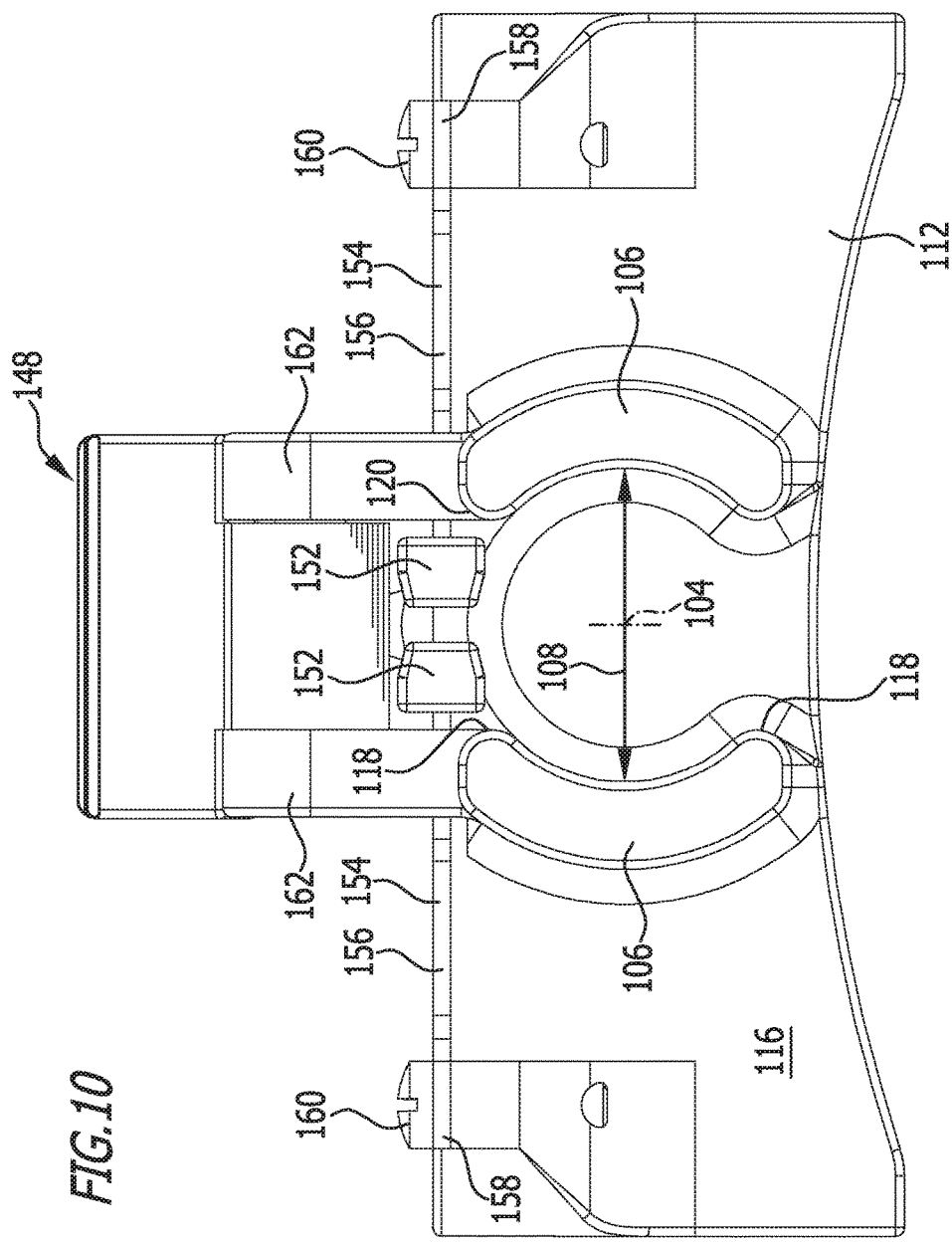
FIG. 10 shows a view of the saw template from FIG. 9, in the direction of the arrow B.

Further arranged on the holding arrangement 14 is an interface 70 for a medical referencing arrangement 72. It is arranged or constructed on a holding bracket 74 that is connected to the cross piece 58. The interface 70 is constructed in the form of a first connecting element 76 which is constructed to correspond to a second connecting element 78 of the referencing arrangement 72. In a connected position, as illustrated schematically in FIG. 7, the connecting elements 76 and 78 engage with one another. They may selectively be disengaged, in which case they adopt a cleaning position.

The first connecting element 76 is constructed in the form of a connecting projection 80, and the second connecting element 78 is constructed in the form of a connection receptacle that corresponds to the connecting projection 80. As an alternative, the first connecting element 76 may also be constructed in the form of a connection receptacle which, in the connected position, engages with force locking and/or positive locking with a corresponding connecting projection on the referencing arrangement 72.

The referencing arrangement 72 includes a substantially cross-shaped carrier 82 which bears at each of the free ends a marker element 84. The marker elements 84, four in total, may selectively be constructed in the form of passive marker elements that reflect electromagnetic radiation or ultrasound, or in the form of active marker elements that emit electromagnetic radiation or ultrasound.

A position of the referencing arrangement 72 may be determined by a medical navigation system 86 that includes at least one detector 88, by means of which radiation that is reflected or emitted by the marker elements 84 can be detected.

The holding arrangement 14 further bears a first coupling element 90 of a coupling arrangement which as a whole is designated by the reference numeral 92, for coupling the holding arrangement 14 and the saw template 16 to one another. A second coupling element 94 of the coupling arrangement 92 is arranged on the saw template 16.

The first coupling element 90 is constructed in the form of a joint ball 96, and the second coupling element 94 is constructed in the form of a joint ball receptacle 98. In this way, the coupling arrangement 92 as a whole comprises a ball joint 100.

If the first and second connecting elements 76 and 78 are separated from one another, they adopt the cleaning position defined above. For example, in FIG. 1 the first connecting element 76 is not coupled to the second connecting element 78.

The coupling arrangement 92 is constructed such that, in an adjustment position, the saw template 16 and the holding arrangement 14 are mounted on one another such that they are displaceable in relation to one another. In order to achieve this, the joint ball receptacle 96 defines a hollow cylindrical or substantially hollow cylindrical internal contour 102. An internal diameter 108 that is predetermined by the internal contour 102 is adapted to an external diameter 110 of the joint ball 96 such that, in the adjustment position, the joint ball 96 is displaceable parallel to a coupling element longitudinal axis 104 that is defined by the second coupling element 94, relatively deeply in relation to one another.

The joint ball receptacle 98 includes two hollow cylindrical wall portions 106 that are substantially diametrically opposite one another and define the internal diameter 108, which corresponds to the external diameter 110 of the joint ball 96 or is smaller by an insubstantial amount.

The wall portions 106 project at a right angle from a substantially cuboid saw template base body, called the saw block 112 below, of the saw template 16. The saw block 112 further includes the guide slot 18, which passes through the saw block 112 parallel to an upper side 114 thereof. Between the two wall portions 106, which project away from a lower side 116 of the saw block 112, there are constructed two gaps 118 that are diametrically opposite each other and whereof one forms a coupling gap 120.

The two wall portions 106 define a linear guide for the joint ball 96, which is moreover rotatable about its centre point, defining a point of rotation 122 of the ball joint 100, between the wall portions 106. This in particular makes it possible not only to displace the saw template 16 in relation to the holding arrangement 14 parallel to the coupling element longitudinal axis 104, but also to pivot it in relation to the holding arrangement 14 about any number of pivot axes 124 that run through the point of rotation 122, or to rotate it about the point of rotation 122. Thus, overall a relative movement between the holding arrangement 14 and the saw template 16 is possible in at least four degrees of freedom of movement.

Thus, the coupling arrangement 92 is constructed such that, in the adjustment position, the saw template and the holding arrangement 14 are mounted on one another, pivotally with respect to one another about a pivot axis.

This allows the first and second coupling elements 90 and 94 to be brought into engagement in a simple manner in that a narrowed portion 126 or a connecting web 128, which in the adjustment position pass through the coupling gap 120 of the joint ball receptacle 98, is constructed between the first coupling element 90 and the holding arrangement base body 54, in particular the second coupling element 36. This is illustrated schematically in FIG. 11, for example.

The coupling gap 120 is preferably wider than an external dimension of the connecting web 128, such that the saw template 16 is rotatable relative to the holding arrangement 14, in particular about the coupling element longitudinal axis 104.

Constructed on the saw template 16, in particular on the saw block 112 thereof, there are further two securing element receptacles 130 in the form of apertures 132 that are not oriented parallel to one another. The apertures 132 are constructed in the form of bores 134 whereof the longitudinal axes 136 do not run parallel, preferably being skewed in relation to one another. Bone securing arrangements 138 in the form of bone pins 140 may be passed through the securing element receptacles 130 in order to fix the saw block 112 firmly to a bone 142 in a defined manner.

Arranged on the upper side 114 is a further interface 70 for a referencing arrangement 72, having a connecting projection 80 whereof the longitudinal axis runs transversely to a plane defined by the upper side 114. The interface 70 makes it possible to couple the saw template 16 to a further referencing arrangement 72, as illustrated schematically in FIG. 7. This makes it possible in particular to determine a position of the saw template 16 in space by the navigation system 86. In particular, in this way relative movements and orientations between the referencing arrangements 72, which are connected on the one hand to the holding arrangement 14 and on the other to the saw template 16, may also be determined with a high degree of precision.

Hitherto, the coupling arrangement 92 has been described only such that a relative movement of the holding arrangement 14 and the saw template 16 is possible in the adjustment position. However, the guide device 10 also further includes a fixing arrangement 144 for holding the holding arrangement 14 and the saw template 16 with force locking and/or positive locking, in a sawing position. In this, the holding arrangement 14 and the saw template 16 are held immovably against one another.

The fixing arrangement 144 may in particular be constructed in the form of a latching and/or snap-fitting connection. In the Figures, a fixing arrangement 144 is constructed by way of example in the form of a clamping arrangement 146.

The fixing arrangement 144 includes a first fixing element 148 which, in the sawing position, presses the first coupling element 90 against the second coupling element 94. In the exemplary embodiment illustrated in the Figures, a clamping force is transmitted indirectly from the first fixing element 148 to the first coupling element 90. For this purpose, the fixing arrangement 144 includes two second fixing elements 150 in the form of elongate, cuboid rods 152 which are each held firmly against the saw block 112 by way of a spring element 154 in the form of a leaf spring 156. For this purpose, a free end 158 of each leaf spring has a bore through it and is screwed to the saw block 122 by a screw 160.

At their end remote from the end 158, the leaf springs 156 bear the rods 152. The leaf spring elements 156 are oriented to face one another, wherein the rods 152 project therefrom transversely, substantially perpendicular to longitudinal axes defined by the spring elements 154. The second fixing elements 150 are arranged parallel to one another in the gap 118 that lies opposite the coupling gap 120. The rods 152 thus define a part of the internal contour 102 of the joint ball receptacle 98.

Projecting from each of the wall portions 106 is a substantially cuboid bearing body 162, which is provided with a bore 164. The bores 164 are oriented coaxially with respect to one another and a cylindrical bearing pin 166 passes through them.

Mounted pivotally on the bearing pin 166 is an eccentric body 168 in the form of a cylinder extending between the bearing bodies 162. The bore 170 passes through the eccentric body 168, the longitudinal axis thereof running eccentrically in relation to a longitudinal axis of the eccentric body 168. The eccentric body 168 is thus pivotal about an eccentric pivot axis 172 that is defined by the bearing pin 166. The eccentric pivot axis runs transversely in relation to the coupling element longitudinal axis 104 and parallel to the guide slot 18.

The first fixing element 148 further includes an actuating member 174, which is in the form of a flat cuboid projection 176 projecting from the eccentric body 168.

Figure 11:
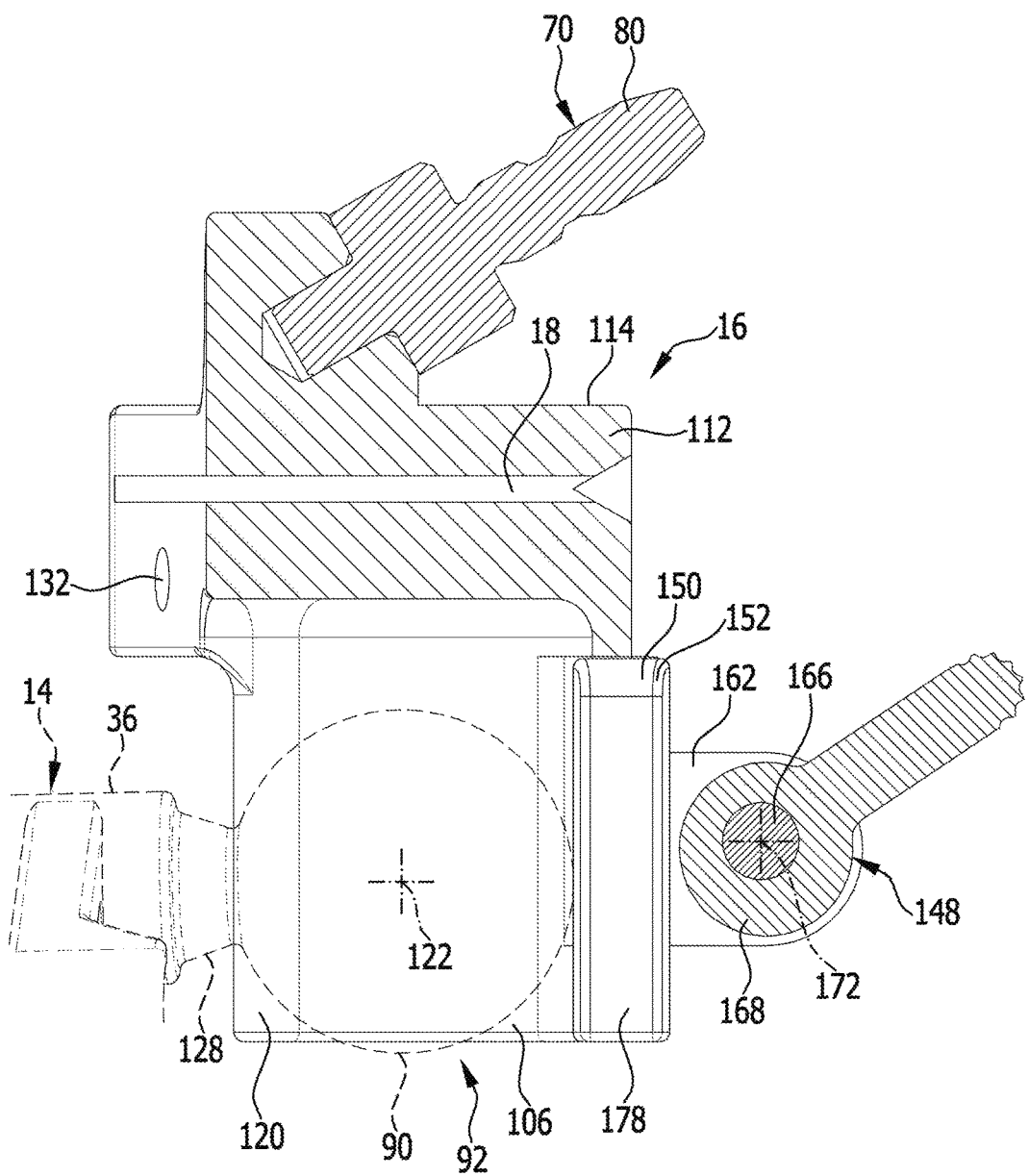
FIG. 11 shows a sectional view along the line 11-11 in FIG. 9, wherein the medical guide device has adopted the adjustment position.
Figure 12:
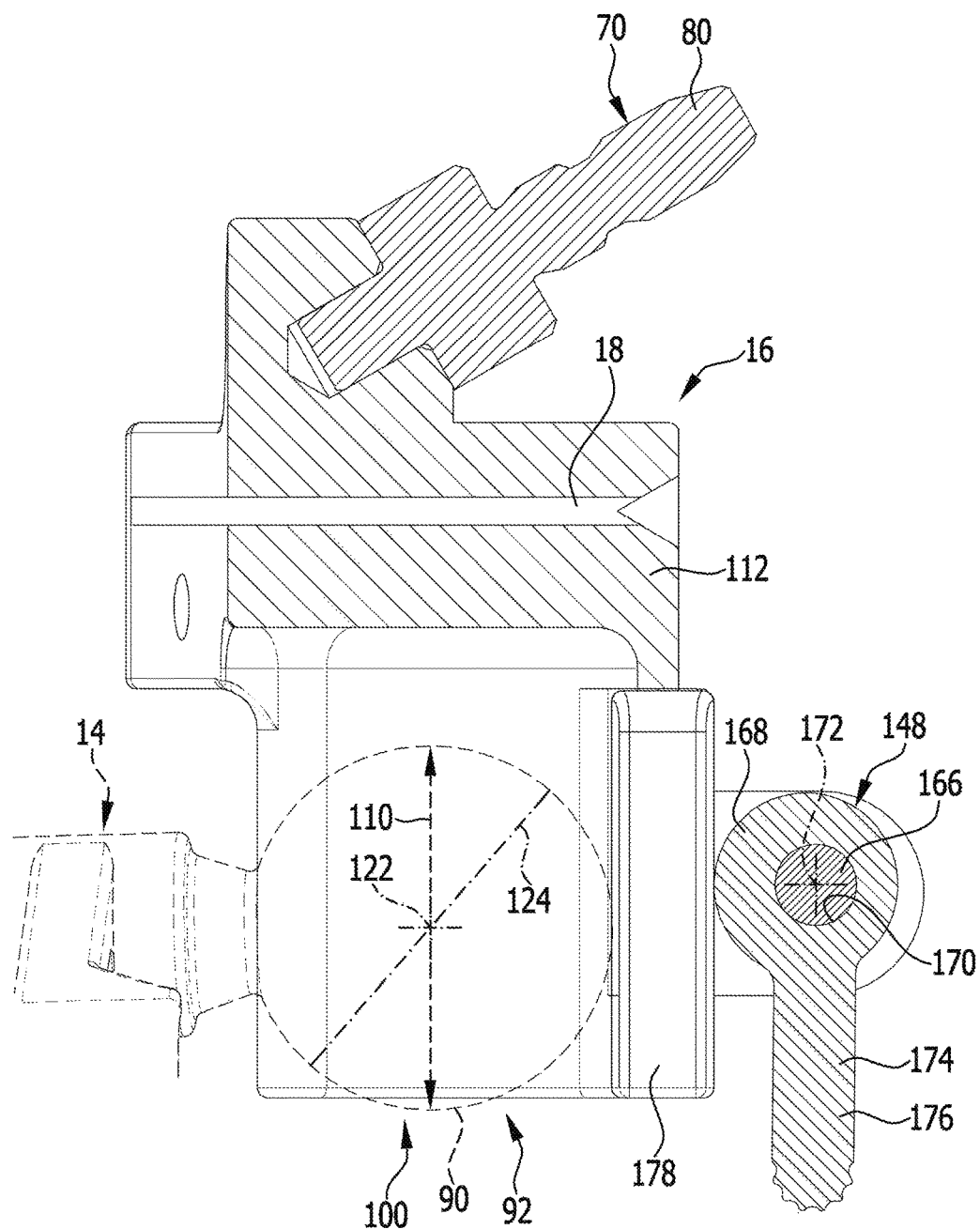
FIG. 12 shows a sectional view similar to FIG. 11, wherein the medical guide device has adopted the sawing position.

If the second fixing element 150 is pivoted out of the adjustment position, illustrated in FIG. 11, into the sawing position, the eccentric body 168 presses increasingly against the rods 152 defining contact pressure bodies 178, the contact pressure body longitudinal axes 180 whereof run parallel to the coupling element longitudinal axis 104. During this, the contact pressure bodies 178 are pressed against the joint ball 96.

The spring elements 154 are constructed such that the contact pressure bodies 178 are already biased towards the joint ball 96, without any action of the eccentric body 168. Thus, the saw template 16 is already held clamped against the holding arrangement 14, at least by a defined clamping force, without the action of the eccentric body 168. By pivoting the second fixing element 150 appropriately, the contact pressure force that is transmitted by way of the contact pressure bodies 178 to the first and second coupling elements 90 and 94 may be increased continuously until the saw template 16 and the holding arrangement 14 are no longer movable in relation to one another.

Use of the medical guide device 10 is explained briefly below.

First, the positioning arrangement 12 is brought into abutment, by means of the bone abutment surfaces 22, against corresponding bone surfaces 182 of the bone 142, for example against bone surfaces 182 of a tibia that face towards a femur bone (not illustrated). In this context, the holding arrangement 14 may already be coupled to the positioning arrangement 12. If not, the second coupling element 36 is clipped into the coupling element receptacle 52. In this context, the gaps 50 serve in particular to receive the limbs 56. Once the holding arrangement 14 is coupled to the positioning arrangement 12, it may be rotated in relation to the positioning arrangement 12, about the longitudinal axis defined by the circular cylinder 48.

In a next step, the holding arrangement 14 is fixed to the bone 142 using the two bone screws 68, and then the positioning arrangement 12 is released from the holding arrangement 14 again. In a next step, the saw template 16 is coupled to the holding arrangement 14. For this purpose, the joint ball receptacle 98 is guided over the joint ball 96, such that the connecting web 128 passes through the coupling gap 120.

If both the holding arrangement 14 and the saw template 16 are connected to a referencing arrangement 72, their positions and/or orientations in space may be determined by the navigation system 86. This allows the saw template 16 to be oriented for making a saw cut on the bone 142, as desired and with a high degree of precision. This is performed by a corresponding displacement and/or pivoting movement of the saw template 16 in relation to the holding arrangement 14, in the adjustment position. Once the saw template 16 has adopted the desired position and orientation, the saw template 16 is secured immovably on the holding arrangement 14 by pivoting the first fixing element 148 of the fixing arrangement 144.

In order to prevent movement of the saw template 16 in relation to the bone 142 when a saw blade is guided through the guide slot 18, the bone pins 140 may selectively be driven through the bores 134 and into the bone 142.

After the bone 142 has been worked on, using a preferably oscillating bone saw, the saw template 16 is released from the bone 142 again by removing the bone pins 140. The saw template 16 can then be released from the holding arrangement 14 by transferring the fixing arrangement 144 back from the sawing position to the adjustment position, by pivoting back the first fixing element 148.

After the saw template 16 has been removed from the holding arrangement 14, the bone screws 68 are withdrawn from the bone 142 again and the holding arrangement 14 is removed.

Figure 13:
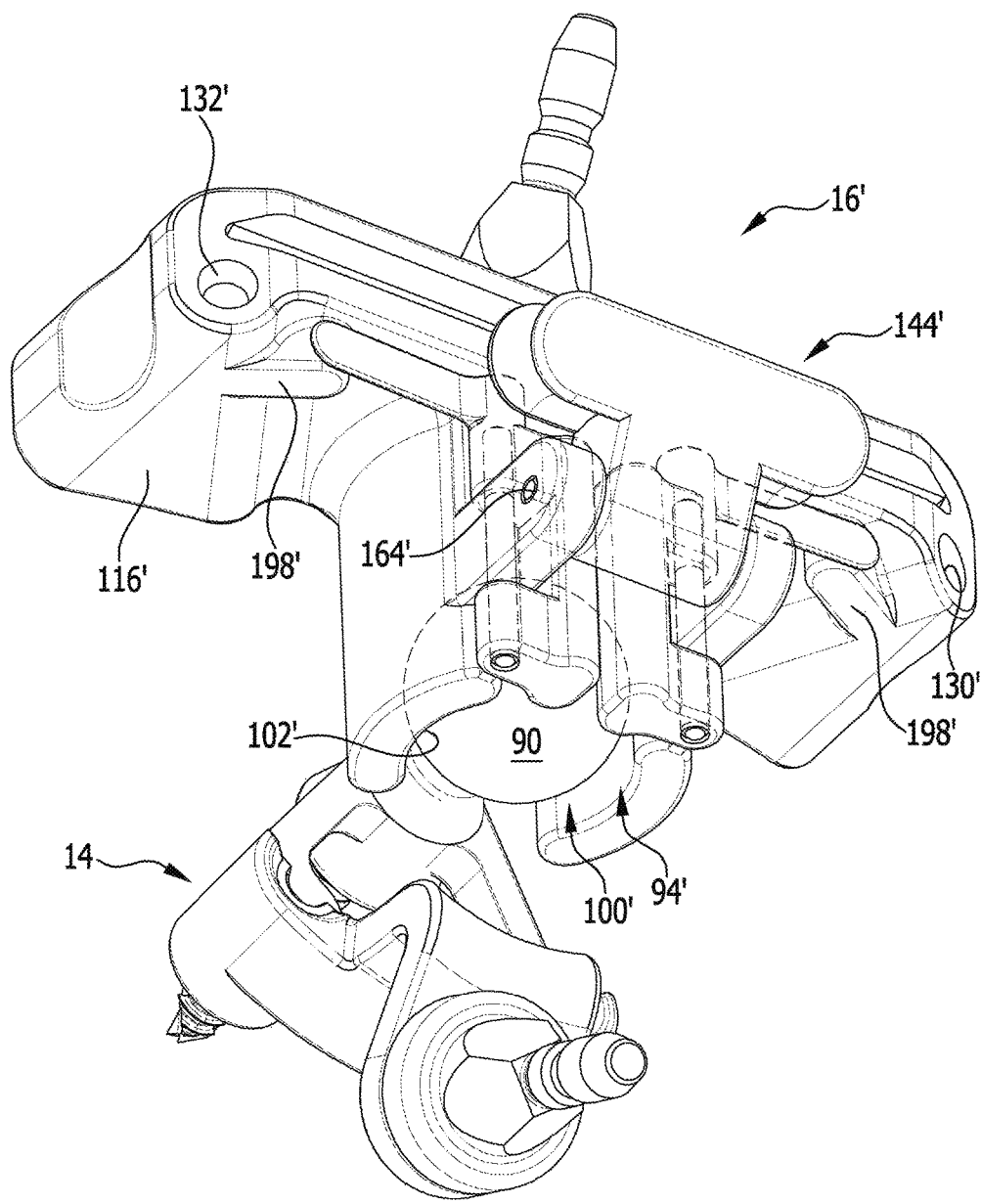
FIG. 13 shows a partly transparent perspective view of the holding arrangement with, coupled thereto, a second exemplary embodiment of a saw template in the sawing position.
Figure 14:
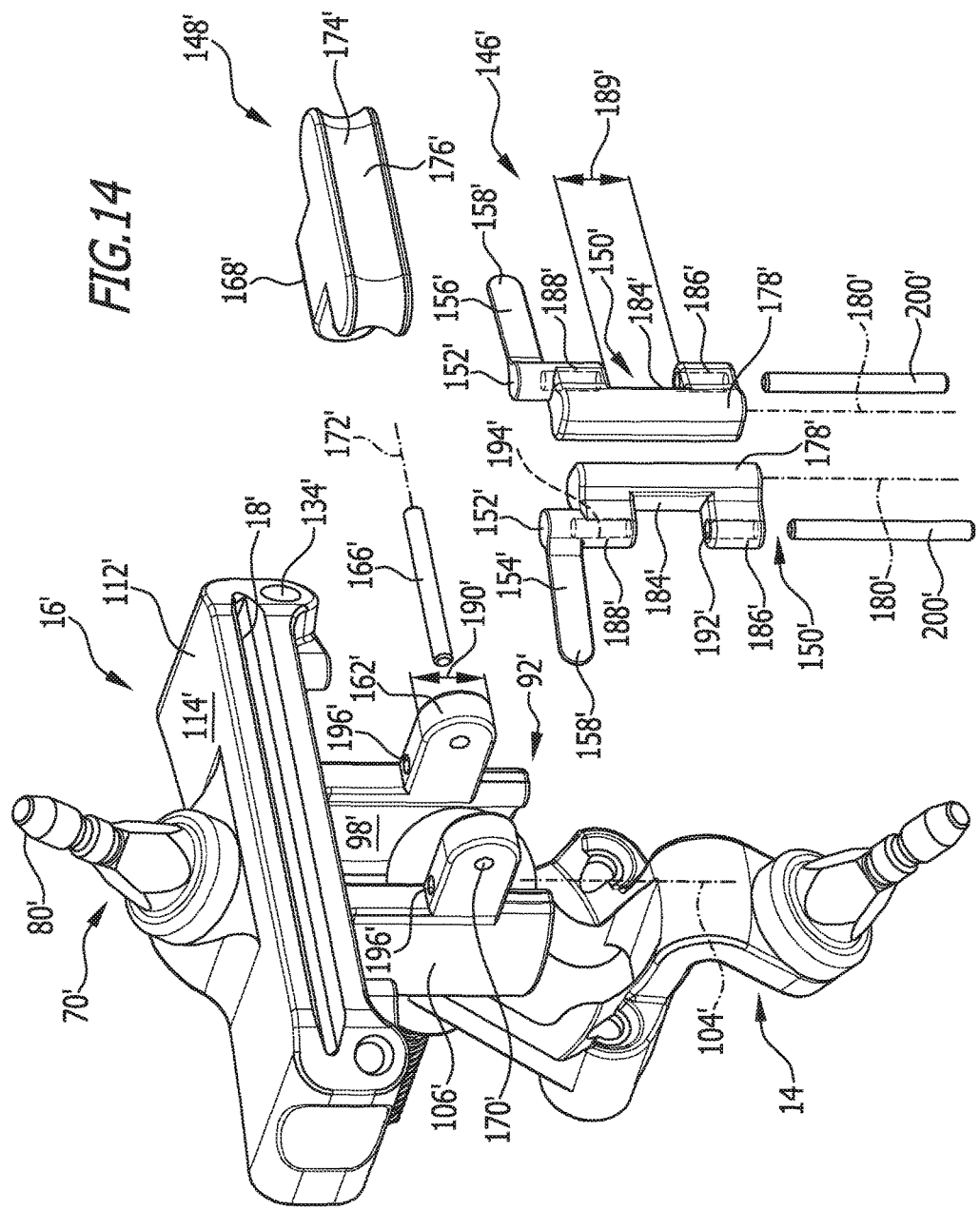
FIG. 14 shows a partly exploded illustration of the arrangement from FIG. 13.

FIGS. 13 and 14 illustrate by way of example a second exemplary embodiment of a saw template, which is designated as a whole by the reference numeral 16', coupled to the holding arrangement 14, in the adjustment position.

As regards its fundamental construction, the saw template 16' does not differ from the saw template 16. For this reason, only the substantial differences between the saw template 16' and the saw template 16 are briefly explained below. In this context, to identify parts of the saw template 16' that are identical to or correspond to parts of the saw template 16, reference numerals with a prime thereafter will be used.

The fixing arrangement 144' of the saw template 16' includes a first fixing element 148' which, in the sawing position, presses the first coupling element 90 against the second coupling element 94'. With the saw template 16' too, a clamping force is transmitted indirectly from the first fixing element 148' to the first coupling element 90. For this purpose, the fixing arrangement 144' likewise includes two second fixing elements 150' in the form of elongate cuboid rods 152', which, on sides 184' facing away from one another, each bear a bearing body 186' and a bearing body 188'. A spacing 189' between the bearing blocks 186' and 188' that are constructed on a rod 152' corresponds to a height 190' of the bearing bodies 162'.

Moreover, the bearing block 186' is provided with a through bore 192', and the bearing block 188' is provided with a blind bore 194' that is open in the direction of the through bore 192', is aligned with the through bore 192' and runs parallel to the contact pressure body longitudinal axes 180'.

Parallel to the coupling element longitudinal axis 104', the bearing bodies 162' are provided, in addition to the bores 164', with a respective bore 196', wherein longitudinal axes of these run at a right angle to one another but do not intersect one another.

The bearing blocks 188' project somewhat beyond an end of the rods 152' that is directed towards the saw block 112'. In this region, a spring element 154' in the form of a leaf spring 156' is integrally formed on each bearing block 188'.

At the point where on the saw template 16 bores provided with an internal thread are constructed for engaging with the screws 160, in the case of the saw template 16' projections 198' that point obliquely in the direction of the bearing blocks 188' are constructed and serve as limit stops for free ends 158' of the leaf springs 156'.

Unlike the free ends 158 in the case of the saw template 16, the free ends 158' are not fixed to the projections 198'. In order nonetheless to achieve defined positioning and movement of the contact pressure bodies 178', the rods 152' are coupled pivotally to the bearing bodies 162'. For this there serve bearing pins 200' which engage by their one end in the blind bore 194' in the bearing block 188' and pass through both the bore 196' in the bearing body 162' and the through bore 192' in the bearing block 186'. In this way, longitudinal axes of the bearing pins 200' define pivot axes about which the contact pressure bodies 178' are pivotal.

By pivoting the first fixing element 148', the first coupling element 90 can be clamped in the joint ball receptacle 98'. In this context, the rods 192', which are already biased resiliently in the adjustment position against the joint ball 96, abut in clamping manner against the first coupling element 90.

Otherwise, the structural composition of the saw template 16' differs only insubstantially from the saw template 16, so in respect of the functioning of the saw template 16', and in particular to avoid repetition, reference can be made to the statements above regarding functioning of the saw template 16.

LIST OF REFERENCE NUMERALS

10 Medical guide device
12 Positioning arrangement
14 Holding arrangement
16, 16' Saw template
18, 18' Guide slot
19 Coupling body
20 Bone abutment element
22 Bone abutment surface
24 Cross piece
26 Abutment body
28 Holding tab
30 Aperture
32 First coupling element
34 Coupling arrangement
36 Second coupling element
38 Latching and/or snap-fitting connecting arrangement
40 Holding body
42 Abutment surface
44 Leaf spring elements
46 End
48 Circular cylinder
50 Gap
52 Coupling receptacle
54 Holding arrangement base body
56 Limb
58 Cross piece
60 Cylindrical body
62 Bore 64 Securing element receptacle
66 Securing element
68 Bone screw
70, 70' Interface
72 Referencing arrangement
74 Holding bracket
76 First connecting element
78 Second connecting element
80, 80' Connecting projection
82 Carrier
84 Marker element
86 Navigation system
88 Detector
90 First coupling element
92, 92' Coupling arrangement
94, 94' Second coupling element
96 Joint ball
98, 98' Joint ball receptacle
100, 100' Ball joint
102, 102' Internal contour
104, 104' Coupling element longitudinal axis
106, 106' Wall portion
108 Internal diameter
110 External diameter
112, 112' Saw block
114, 114' Upper side
116, 116' Lower side
118 Gap
120 Coupling gap
122 Point of rotation
124 Pivot axis
126 Narrowed portion
128 Connecting web
130, 130' Securing element receptacle
132, 132' Aperture
134, 134' Bore
136 Longitudinal axis
138 Bone securing arrangement
140 Bone pin
142 Bone
144, 144' Fixing arrangement
146, 146' Clamping arrangement
148, 148' First fixing element
150, 150' Second fixing element
152, 152' Rod
154, 154' Spring element
156, 156' Leaf spring
158, 158' End
160 Screw
162, 162' Bearing body
164, 164' Bore
166, 166' Bearing pin
168, 168' Eccentric body
170, 170' Bore
172, 172' Eccentric pivot axis
174, 174' Actuating member
176, 176' Projection
178, 178' Contact pressure body
180, 180' Contact pressure body longitudinal axis
182 Bone surface
184' Side surface
186' Bearing block
188' Bearing block
189' Spacing
190' Height
192' Through bore
194' Blind bore
196' Bore
198' Projection
200' Bearing pin

What is claimed is:

1. A medical guide device for working on a bone, comprising:
a holding arrangement, which is holdable firmly against a bone, for holding the guide device firmly against the bone, and
a saw template with a guide slot for a saw blade,
the holding arrangement and the saw template engaging with one another and being arranged to be movable in relation to one another in an adjustment position,
the holding arrangement and the saw template being movable from the adjustment position into a sawing position in which they are held firmly and immovably in relation to one another,
the guide device comprising a coupling arrangement for coupling the holding arrangement and the saw template in the adjustment position and in the sawing position,
the coupling arrangement comprising first and second coupling elements which are arranged or constructed on the holding arrangement and on the saw template respectively, which are in engagement with one another in the adjustment position, and which are held against one another with at least one of force locking and positive locking in the sawing position,
wherein:
the first coupling element is constructed in a form of a joint ball, and
the second coupling element is constructed in a form of a joint ball receptacle, the joint ball receptacle forming a hollow cylindrical or substantially hollow cylindrical internal contour.

2. The medical guide device according to claim 1, wherein at least one of:
(a) an interface for a medical referencing arrangement whereof at least one of the position and orientation in space is detectable by a medical navigation system, the interface being arranged or constructed at least one of on the holding arrangement and on the saw template, and
(b) a medical referencing arrangement whereof at least one of the position and orientation in space is detectable by a medical navigation system, the medical referencing arrangement being arranged or constructed at least one of on the holding arrangement and the saw template.

3. The medical guide device according to claim 2, wherein at least one of:
(a) the interface is constructed in a form of a first connecting element which is constructed to correspond to a second connecting element of the medical referencing arrangement, and the first and the second connecting elements being in engagement in a connected position and disengaged in a cleaning position, and
(b) the medical referencing arrangement bears at least one marker element whereof the position in space is detectable by a medical navigation system.

4. The medical guide device according to claim 1, wherein at least one of:
(a) the coupling arrangement is constructed such that, in the adjustment position, the saw template and the holding arrangement are mounted on one another such that they are displaceable in relation to one another, and (b) the second coupling element defines a coupling element longitudinal axis, and wherein, in the adjustment position, the saw template and the holding arrangement are mounted on one another such that they are displaceable in relation to one another parallel to the coupling element longitudinal axis,
and
(c) the coupling arrangement is constructed such that, in the adjustment position, the saw template and the holding arrangement are mounted on one another such that they are pivotal in relation to one another about a pivot axis.

5. The medical guide device according to claim 1, wherein the coupling arrangement is constructed such that, in the adjustment position, the saw template and the holding arrangement are mounted on one another such that they are rotatable in relation another about an axis of rotation.

6. The medical guide device according to claim 1, wherein:
the holding arrangement has a holding arrangement base body, and
the first coupling element is held on the holding arrangement base body.

7. The medical guide device according to claim 6, wherein:
a narrowed portion or a connecting web is constructed between the first coupling element and the holding arrangement base body, and
in the adjustment position and the coupling position, the narrowed portion or connecting web passes through a coupling gap in the joint ball receptacle.

8. The medical guide device according to claim 1, further comprising a fixing arrangement for holding the holding arrangement and the saw template in the sawing position with at least one of force locking and positive locking.

9. The medical guide device according to claim 8, wherein the fixing arrangement at least one of:
(a) is constructed in a form of at least one of a latching, snap-fitting and clamping arrangement,
and
(b) includes at least one first fixing element which, in the sawing position, presses the first coupling element directly or indirectly against the second coupling element.

10. The medical guide device according to claim 9, wherein:
the fixing arrangement includes at least one second fixing element, and
in the sawing position, the at least one first fixing element presses the at least one second fixing element against the first coupling element and presses the first coupling element against the second coupling element.

11. The medical guide device according to claim 10, wherein the at least one second fixing element includes at least one of:
(a) a leaf spring element that is arranged or constructed on the saw template,
and
(b) a contact pressure body.

12. The medical guide device according to claim 11, wherein at least one of:
(a) the leaf spring element bears, at a free end or in a region of the free end, the contact pressure body,
and
(b) the contact pressure body defines a contact pressure body longitudinal axis that runs parallel or substantially parallel to a coupling element longitudinal axis.

13. The medical guide device according to claim 10, wherein the at least one second fixing element is at least one of:
(a) arranged or constructed to be movable on the saw template,
and
(b) held in a gap or a recess between at least two hollow cylindrical wall portions of the joint ball receptacle, the at least two hollow cylindrical wall portions define an internal diameter that corresponds or substantially corresponds to an external diameter of the joint ball.

14. The medical guide device according to claim 9, wherein the at least one first fixing element includes an eccentric body that is pivotal about an eccentric pivot axis.

15. The medical guide device according to claim 14, wherein at least one of:
(a) the eccentric axis runs transversely to a coupling element longitudinal axis,
and
(b) the eccentric axis runs parallel or substantially parallel to the guide slot,
and
(c) the at least one first fixing element includes an actuating member, the actuating member being arranged or constructed so as to project away from the eccentric body.

16. The medical guide device according to claim 1, wherein at least one securing element receptacle for a bone securing arrangement is arranged or constructed at least one of on the holding arrangement and the saw template.

17. The medical guide device according to claim 16, wherein at least one of:
(a) the at least one securing element receptacle is constructed in the form of an aperture, and
(b) the holding arrangement has at least two securing element receptacles with longitudinal axes that run parallel or substantially parallel to one another, and
(c) the saw template has at least two securing element receptacles with longitudinal axes that run in a manner inclined with respect to one another.

18. The medical guide device according to claim 1, further comprising a positioning arrangement which is coupled to the holding arrangement in a positioning disposition.

19. The medical guide device according to claim 18, wherein:
the positioning arrangement includes at least one bone abutment element having a bone abutment surface and at least one first coupling element of a coupling arrangement,
in the positioning disposition, the at least one first coupling element is in engagement with at least one of force and positive locking with at least one second coupling element of the coupling arrangement that is arranged or constructed on the holding arrangement.

20. The medical guide device according to claim 19, wherein:
the at least one second coupling element is constructed in a form of a cylindrical coupling body which bears or includes the first coupling element, and
the at least one first coupling element is constructed in a form of a coupling receptacle corresponding to the coupling body.

21. The medical guide device according to claim 1, wherein the joint ball receptacle includes at least two hollow cylindrical wall portions that define an internal diameter that corresponds or substantially corresponds to an external diameter of the joint ball.

22. The medical guide device according to claim 21, wherein the joint ball receptacle includes two hollow cylindrical wall portions which are arranged diametrically opposite one another.

* * * * *